United States Patent
Mead et al.

(10) Patent No.: US 7,057,724 B1
(45) Date of Patent: Jun. 6, 2006

(54) PARTICULATE INFO TO FIELD UNITS

(75) Inventors: Donald Mead, Carlsbad, CA (US); Gregory Quist, Escondido, CA (US)

(73) Assignee: Institute of Critical Care Medicine, Rancho Mirage, CA (US)

( * ) Notice: Subject to any disclaimer, the term of this patent is extended or adjusted under 35 U.S.C. 154(b) by 275 days.

(21) Appl. No.: 10/393,459

(22) Filed: Mar. 20, 2003

Related U.S. Application Data

(60) Provisional application No. 60/366,700, filed on Mar. 21, 2002.

(51) Int. Cl.
*G01N 21/00* (2006.01)

(52) U.S. Cl. .................................................... 356/343

(58) Field of Classification Search ........ 356/335–344; 435/287.1–287.8, 6, 7.1; 422/55, 58, 67
See application file for complete search history.

(56) References Cited

U.S. PATENT DOCUMENTS

| | | | |
|---|---|---|---|
| 3,770,351 A | 11/1973 | Wyatt | |
| 3,901,602 A | 8/1975 | Gravatt et al. | |
| 4,070,113 A | 1/1978 | Frazer et al. | |
| 4,173,415 A | 11/1979 | Wyatt | |
| 4,265,538 A | 5/1981 | Wertheimer | |
| 4,548,500 A | 10/1985 | Wyatt et al. | |
| 4,565,448 A | 1/1986 | Abbott et al. | |
| 4,702,598 A | 10/1987 | Böhmer | |
| 4,728,190 A | 3/1988 | Knollenberg | |
| 4,906,094 A | 3/1990 | Ashida | |
| 4,907,884 A | 3/1990 | Philips et al. | |
| 4,942,305 A | 7/1990 | Sommer | |
| 4,952,055 A | 8/1990 | Wyatt | |
| 4,987,539 A | 1/1991 | Moore et al. | |
| 5,125,737 A | 6/1992 | Rodriguez et al. | |
| 5,247,340 A | 9/1993 | Ogino | |
| 5,305,071 A | 4/1994 | Wyatt | |

(Continued)

FOREIGN PATENT DOCUMENTS

GB 2317228 A 3/1998

OTHER PUBLICATIONS

"Recent Overview Article—Aerosol Characterization Research at the University of Hertfordshire", by Prof. Paul Kaye, STRC Particle Instruments Research Group, Science and Technology Research Centre,University of Hertfordshire, Hatfield, United Kingdom, reproduced from the Aerosol Society Newsletter, No. 33, Sep. 18-20, 1998.

(Continued)

*Primary Examiner*—Tu T. Nguyen
(74) *Attorney, Agent, or Firm*—Leon D. Rosen

(57) ABSTRACT

An improvement in a system that includes a group of field units (10, 10A) that each identifies unknown microscopic particles by use of a computer that compares an unknown particle interrogation pattern to the interrogation patterns of a set of known species of particles, which facilitates upgrading of the group of field units. Each field unit is connected by a communication link (84) to a central station (80). The central station can send interrogation patterns of a new species of particle to the field unit computers, which store them in a known-species-particle memory (34) that holds patterns of previously known species of particles. The field unit stores the patterns of unidentified particles in a memory (90) and notifies the central station when it has detected an invasion of a new species.

7 Claims, 2 Drawing Sheets

U.S. PATENT DOCUMENTS

| | | |
|---|---|---|
| 5,414,508 A | 5/1995 | Takahashi et al. |
| 5,436,465 A | 7/1995 | Borden et al. |
| 5,534,999 A | 7/1996 | Koshizuka et al. |
| 5,627,040 A | 5/1997 | Bierre et al. |
| 5,737,078 A | 4/1998 | Takarada et al. |
| 5,999,256 A | 12/1999 | Jones et al. |
| 6,023,324 A | 2/2000 | Myers |
| 6,100,541 A | 8/2000 | Nagle et al. |
| 6,118,531 A | 9/2000 | Hertel et al. |
| 6,120,734 A | 9/2000 | Lackie |
| 6,313,908 B1 | 11/2001 | McGill et al. |
| 6,421,121 B1 | 7/2002 | Haavig et al. |
| 6,713,298 B1 * | 3/2004 | McDevitt et al. ........ 435/287.8 |

OTHER PUBLICATIONS

"Discrimination of phytoplankton via light-scattering properties", by Philip J. Wyatt and Christian Jackson, Limnology And Oceanography, 34(1), 1989, pp. 96-112, American Society of Limnology and Oceanography, Inc.

* cited by examiner

PARTICULATE INFO TO FIELD UNITS

CROSS-REFERENCE TO RELATED APPLICATION

Applicant claims priority from U.S. Provisional Application Ser. No. 60/366,700 filed Mar. 21, 2002.

BACKGROUND OF THE INVENTION

One method for identifying particles in a fluid such as water, is to interrogate each of many particle and produce an interrogation pattern representing characteristics unique to each particle. One example is where a system directs a laser beam through water, and a group of photodetectors detect light scattering by particles passing through a small detect zone lying along the laser beam. The outputs of the photodetectors constitute an interrogation pattern. The interrogation pattern is compared to interrogation patterns of each of a group of known species of particles. If there is a high correlation between the unknown particle interrogation pattern and the patterns of a particular known species, then the unknown particle is deemed likely to be of that species. The interrogations and comparisons are carried out by field units that may continuously sample the water at each of numerous water purification plants.

Occasionally, a new species of particle, such as a new species of pathogenic microorganism, becomes of interest. It is possible to occasionally load interrogation patterns of all species of interest onto a computer disc, carry it to each of the field units, and substitute the new group of patterns for those presently in each field unit memory. However, this would result in considerable delay while a technician visits each of the field units and downloads a new disc into them. This also has the disadvantage that it requires considerable labor of personnel to visit each of the field units, and can result in considerable delay before a new dangerous microorganism begins to be detected.

Sometimes, a new organism is introduced into a water purification plant, as by a change in weather or other conditions resulting in a rapid increase in a particular microorganism. It is desirable that persons in charge of the purification or treatment plants learn about this as soon as possible. It would be desirable if the field units could identify the proliferation of a new species (or a great increase in a species that previously occurred rarely) of microscopic particle and quickly notify the central station.

SUMMARY OF THE INVENTION

In accordance with one embodiment of the present invention, an improvement is provided for upgrading a system where field units are used to identify unknown microscopic particles in a fluid by generating unknown particle interrogation patterns that are each unique to each unknown particle. The unknown particle interrogation pattern is compared to interrogation patterns generated for particles that are each of one of a group of known species. Each field unit is connected by a communication link to a central station. When the central station generates a group of known particle interrogation patterns for particles that are all of the same new species, it transmits the known interrogation patterns to each field unit. The computer of each field unit enters the known particle interrogation patterns for the new species into its memory, and thereafter compares the interrogation pattern of an unknown particle to the known interrogation patterns of all species in its memory including the new one.

Each field unit stores unknown particle interrogation patterns that are not identified as one of a group of known species, as in an unknown-species-pattern memory. The field unit or other computer analyzes the numerous unknown species interrogation patterns to determine whether a significant number of them appear to all be of the same species. This alerts personnel to the fact that a large number of particles of a new species has been introduced into the water system, so the personnel can more throughly examine particles of the new species.

The novel features of the invention are set forth with particularity in the appended claims. The invention will be best understood from the following description when read in conjunction with the accompanying drawings.

DESCRIPTION OF THE PREFERRED EMBODIMENTS

Figure 1:
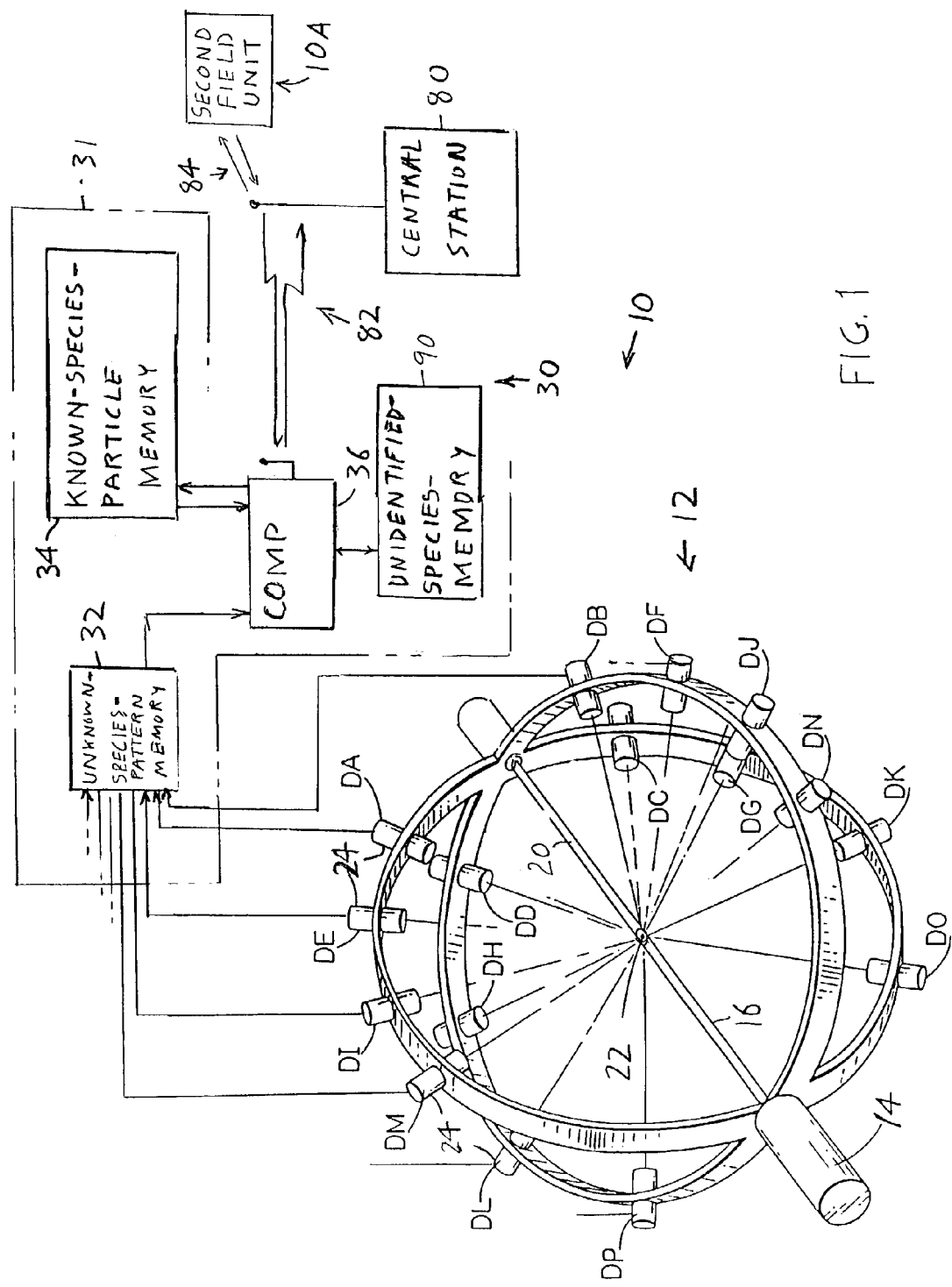
FIG. 1 is a partial isometric view and partial block diagram view of a system of the present invention.

FIG. 1 illustrates a particle monitor system field unit 10 for identifying particles in a fluid such as water or air. The system includes a scatter detector 12 that comprises a light source (from far infrared to far ultraviolet) in the form of a laser 14 that generates a laser beam 16. The laser beam moves along a laser beam path 20. A detect zone 22 is located along the laser beam path. When a microscopic particle passes through the detect zone 22, it scatters light in different directions. The light scattered in different directions is detected by photodetectors 24 that each detects only light from a location at or very close to the detect zone 22 and that is scattered in the direction (e.g. within an angle of 1.5°) of that photodetector. It is noted that each photodetector 24 can include a photocell at each corresponding location shown, or can include a holographic or other device that diffracts or otherwise deflects light as to a linear array of CCD's (charge couple devices). FIG. 1 shows sixteen detectors labeled DA through DP.

In one example, the laser beam has a wavelength of about 0.6 micrometers and the device is intended to detect particles having a diameter of about one to thirty wavelengths. In that example, the detect zone 22 has a width and length that are each about 1.5 mm, and a thickness of about 0.1 mm. If the fluid is moving at a velocity such as 8 cm per second, then each particle may be expected to pass through the detect zone during a period of about 1.5 milliseconds. The passage of each particle downward through the detect zone and its scattering of the laser beam that passes horizontally through the detect zone, is referred to as an "event" or "interrogation". Since the outputs of the multiple photodetectors 24 represent the intensity of light scattered in each of a plurality of known directions from the detect zone, the output of all photodetectors for one event may be referred to as an "eventvector" or "interrogation pattern". The interrogation pattern is raw data before it is compared or interpreted. Each raw data interrogation pattern, which is the output of all photodetectors when a single particle is interrogated, is stored in an unknown-species-pattern memory 32. Until the interrogation pattern is analyzed, the particle is an unknown particle and its interrogation pattern is an unknown interrogation pattern.

Thus, the scatter detector 12 of FIG. 1 interrogates particles of unknown species by detecting light scattered in a plurality of different directions by the particles. Other means for interrogating microscopic particles (those less than about 0.1 mm so they are generally not visible to the naked eye) to generate patterns unique to the particles, may be available. Examples are devices that detect scattering of high frequency sound in different directions, that analyze patterns representing the appearance of a particle as by a facial recognition program, or that detects rate of growth or demise of particles in a predetermined nutrient or toxin bath.

A comparing system 30 implemented by a computer 31, which includes the memory 32 for unknown species raw data interrogation patterns, also includes a known-species-pattern memory 34 that stores a large number of interrogation patterns for a number of known species of particles. Such known interrogation patterns can be generated by using the scatter detector 12, when only particles of a known species are present. The different known interrogation patterns for each known species represent particles of that species in different orientations and particles of that species which are of different kinds as where they vary slightly in size and shape. Instead of using known species interrogation patterns produced by passing only particles of that known species through the scatter detector 12, it is possible to use a computer to generate interrogation patterns. Such computer generated interrogation patterns represent one species at multiple orientations, and for particles of that species that vary somewhat in size and shape. There may be several hundred interrogation patterns for that species.

A comparer 36 compares each unknown particle raw data interrogation pattern stored in the unknown-species-pattern memory 32 to the known particle interrogation patterns stored in the memory 34. The comparer 36 determines whether each unknown pattern is of a species whose patterns are stored in the known-species-particle memory 34, or is not.

Figure 2:
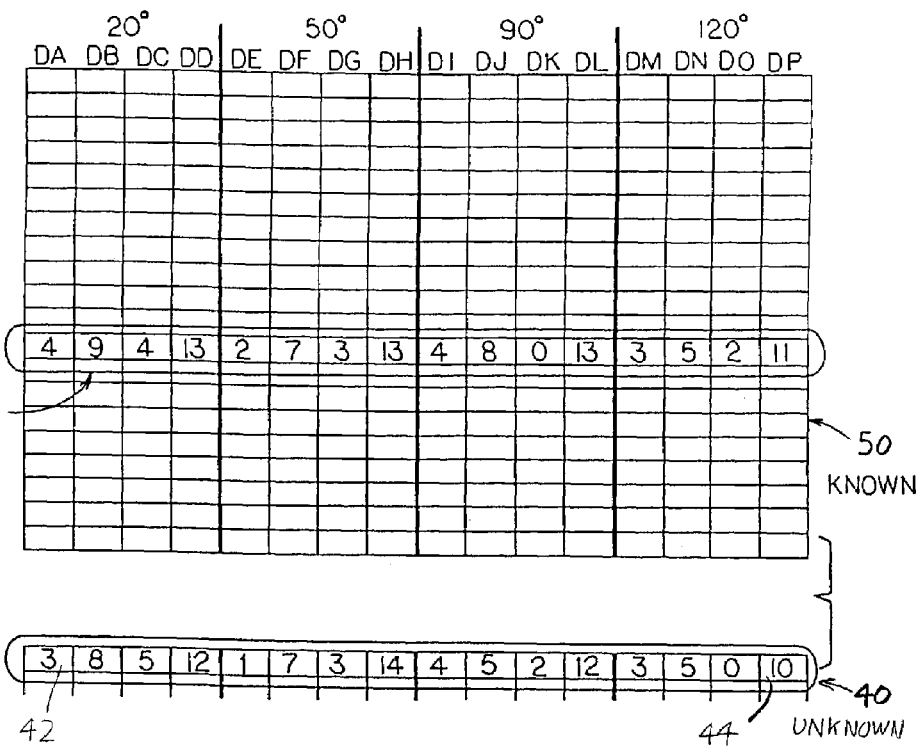
FIG. 2 is a representation of the memory of a field unit of the system of FIG. 1.

FIG. 2 includes a row of memory cells 40 that store one unknown particle interrogation pattern. As mentioned above, the particular detect system has sixteen photodetectors that detect the amplitude of light scattered in each of sixteen different directions from the detect zone 22. The row of cells 40, stores the outputs of the sixteen photodetectors DA-DP as numbers that represent the amplitude of light detected by the photodetectors. The numbers in all sixteen boxes together represent one unknown particle raw data interrogation pattern. It is noted that each number can represent the power of two, so the number "3" in the first box 42 represents $2^3$ which is 8, while the number "10" in the sixteenth box 44 represent $2^{10}$ which is 1024. The numbers stored in the rows 50 of known interrogation patterns represent detections of particles of a known species, and there may be several hundred or thousands of rows of known particle interrogation patterns for each of the species whose patterns are stored in the memory 34.

Figure 3:
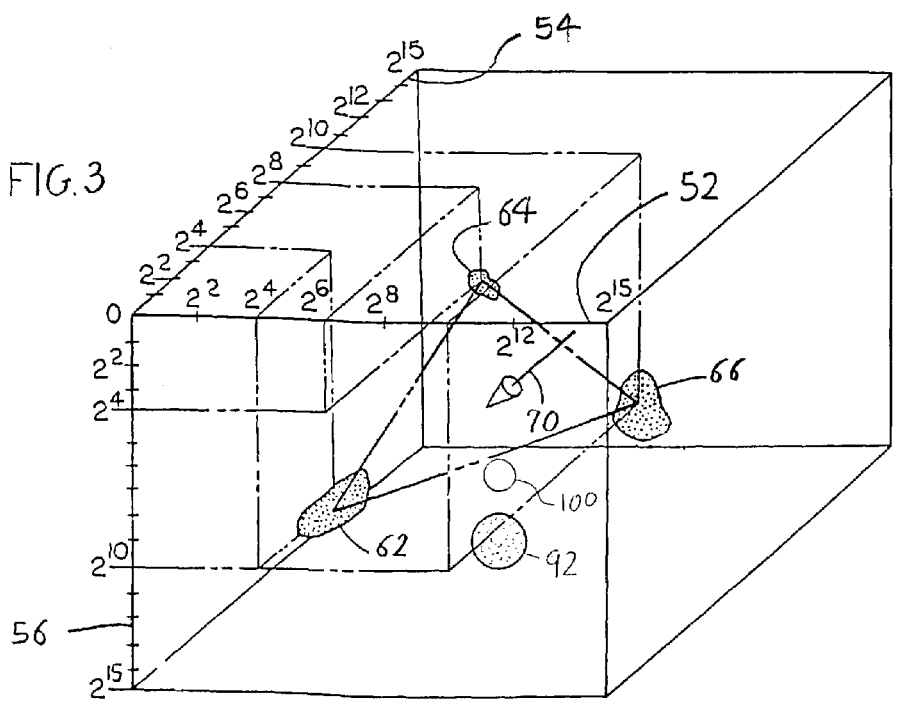
FIG. 3 is a simplified three-dimensional representation of multi-dimensional analysis using the MANOVA analyzing technique of the system of FIG. 1.

The comparer 36 of FIG. 1 is most easily implemented by a computer program such as MANOVA (multiple analysis of variance analysis) which is a program entitled Mat Lab offered by Mat Works located in Nantucket, Mass. FIG. 3 is a simplified example where only three detectors (instead of sixteen) have been used, so each particle interrogation pattern comprises only three numbers that can be arranged in three dimensions. The outputs of the detectors for an interrogation determines the position of each point along each of the three axes 52, 54, 56. In FIG. 3, the interrogation patterns for three different species are each clustered in one of three clusters 62, 64 and 66. When viewed along the direction of arrow 70, the interrogation patterns of each of the three clusters are closest together and the three clusters are spaced furthest apart (compromises are made). When an unknown particle raw data interrogation pattern is detected (and placed in memory 32), the comparer determines wether the unknown particle interrogation pattern falls into one of the known clusters 62, 64, 66 or is outside each of them. If the unknown particle interrogation pattern is outside the known clusters 62–66, then the unknown particle cannot be identified.

As mentioned above, one important application of the present invention is in a water treatment plant, where perhaps a dozen of the scatter detector systems 12 (FIG. 1) are located, which each may be associated with a separate comparing system 30. The entire monitor arrangement field unit 10 may be left untended for long periods of time. However, if certain pathogens are detected at more than a predetermined rate by a monitor arrangement, then an alarm may be produced to alert personnel that the water treatment plant is not operating properly. Also, if one or a given number of known deadly microbes are detected within a short period of time, then another type of alarm may be produced.

The particular species of microorganisms whose particle interrogation patterns are stored in the known-species-pattern memory 34 may occasionally have to be revised. For example, if a new pathogen is found to be contaminating water treatment plants in the region, then the set of perhaps thousands of interrogation patterns for the new microbe may have to be inserted into the memory 34. Although this could be done manually by a technician taking a portable memory such as a memory disc to the multiple comparing systems at each plant, such a manual upgrading has disadvantages. These include the considerable delay until a technician can travel to the treatment plants and upgrade all of the multiple water quality monitor arrangements 10 at each plant, in addition to the time of a technician. To avoid this, applicant provides a central station 80 (FIG. 1) and an electronic link, or communication link 82, 84 between the central station and the comparing systems 30 of the multiple field units 10, 10A that are operating in the field. When it is desirable to add the interrogation patterns for a new known species to the known-species-pattern memory 34, this can be accomplished through the electronic links 82, 84. The link can be a telephone line, a satellite communication, an internet link, or other similar means, and the central station may be located more than one kilometer from the infield unit.

When the computer 31 receives a new set of known particle raw data interrogation patterns, the computer delivers the patterns to the known-species-pattern memory 34. Thereafter, whenever the computer is comparing an unknown particle raw data interrogation pattern, to the known groups of patterns in the memory 34, the computer will compare the unknown raw data interrogation pattern to all groups of patterns stored in the memory 34, including the recently received group of patterns representing a new species that was received from the central station.

There is always a danger that a new pathogen will find its way into water supplies and not be detected until many people become ill. Applicant is able to use the multiple field units such as 10, 10A that are positioned at multiple different locations in each of multiple water treatment plants, to more rapidly detect species of microscopic particles that are new to the area and which may be pathogens. The new species of particles may be a result of weather changes that cause rapid growth of certain species that produce toxins or even by terrorist contamination. The comparer 36 for comparing each unknown particle interrogation pattern with the clusters of known particle interrogation patterns such as 62–66 of FIG. 3 for known species, has a memory 90 (FIG. 1) for recording unknown interrogation patterns that do not fit into one of the known clusters 62–66. Most unknown particle interrogation patterns do not fall into any cluster when viewed along the view direction 70 in FIG. 3. Occasionally, the comparer 36 compares unknown particle interrogation patterns stored in the unknown-species-pattern memory 32 to determine whether a large proportion of the unknown particle interrogation patterns, such as more than one or two percent, fall into a cluster such as indicated at 92 in FIG. 3. Then, the comparer can generate an alarm signal indicating that a possibly new species has been found in the water supply, which is not one of the species whose interrogation patterns are stored in the known-species-pattern memory 34, and that exists at a significant frequency in the water that is being monitored. The "new" species may be a species that turned up only occasionally (e.g. much less than 0.1% of all unknown particles).

In one example, after a predetermined number of unknown particle interrogation patterns are recorded in memory 90 (assuming that those interrogation patterns that were found to be one of the known species were erased from the memory 32 but nor recorded in memory 90), the remaining unknown interrogation patterns are analyzed as a group by the program in comparer 36. The analysis is made to determine whether there is a high density of unknown interrogation patterns that fall into a cluster 92 (FIG. 3) of small volume, comparable to the volume of one of the known species of clusters 62–66. If the density is high, as where the density (percent of all unknown interrogation patterns) in the cluster 92 is more than ten times as high as the density elsewhere in FIG. 3 for the unknown particle patterns, such as around the location 100, this may indicate that a species of particles new to the area has been detected. In that case, the comparer 36 delivers a signal over the link 82 in FIG. 1, to the central station 80 to alert the central station of its finding. Personnel from the central station may immediately analyze the data indicating the presence of a cluster at 92 in FIG. 3, or may wait until several similar clusters are detected by other monitor arrangements 10. Personnel then can analyze water at the location where a new species may be present, by the more conventional processes that take considerable time, to identify the species of the new particle. If a new particle is found that is pathogenic, the central station may deliver a group of known particle interrogation patterns for that new species to the known-species-pattern memories 34 of many other field units such as 10, 10A that are connected to the central station.

While FIG. 1 shows separate memories such as 32, 34, 90 in a computer, it should be noted that modern computers can store all of the data on the same disc or other medium, but with different addresses in the memory.

Thus, the invention provides an apparatus and method for enabling rapid upgrading of particle monitoring arrangements that are operating in the field to provide known particle interrogation patterns for new species of particles. The apparatus and method also enables field units to detect the presence of new species of particles for analysis.

Although particular embodiments of the invention have been described and illustrated herein, it is recognized that modifications and variations may readily occur to those skilled in the art, and consequently, it is intended that the claims be interpreted to cover such modifications and equivalents.

The invention claimed is:

1. In a system for identifying unknown microscopic particles in a fluid, which includes a plurality of field units at different locations, wherein each field unit has an interrogation system that produces raw data interrogation patterns that are each unique to an unknown particle that is interrogated, and each field unit has a field unit computer that attempts to identify those particles as one of a plurality of known species of particles by comparing a raw data interrogation pattern produced during interrogation of the unknown particles with stored interrogation patterns of known species of particles, the improvement wherein:

said field unit computers each has a known-species-patterns memory that stores raw data interrogation patterns produced by each of said known species; and including a central station that is connected through a communication link to said field unit computers, and that transmits signals representing a group of new raw data interrogation patterns for a known new species of microscopic particles, said field unit computer being constructed to receive said signals representing new interrogation patterns for new species and to thereafter add said interrogation patterns to its known-species-patterns memory.

2. The system described in claim 1 wherein:

each of a plurality of said field units has an unidentified-species memory that stores the raw data interrogation patterns of at least some of the unknown particles that are not identified as one of the plurality of known species by the field unit computer;

each of said field unit computers is constructed to analyze the patterns of multiple unidentified particles to determine whether or not the patterns of a group of said multiple unidentified particles are similar enough to each other to indicate the presence of multiple particles of a new species of particle in the fluid.

3. The system described in claim 1 wherein:

said interrogation system comprises a light source that produces a beam of light that passes through said fluid, including a detect zone of limited length along said beam and in said fluid, and a plurality of photodetectors that each detects light scattered in each of a plurality of different directions from said detect zone, with outputs of said plurality of photodetectors comprising an unknown particle raw data interrogation pattern representing the unknown particle, the raw data interrogation patterns of multiple particles of the same known species being stored in said known-species memory, and said computer being constructed to compare the raw data interrogation pattern of said unknown particle to the interrogation patterns stored in said known-species-particle memory.

4. A system for identifying unknown microscopic particles in a fluid, which includes interrogating apparatus that directs a light beam through the fluid and a plurality of photodetectors that detect light scattered in different directions from a detect zone lying along the beam and in the fluid, with the outputs of said plurality of photodetectors constituting a raw data interrogation pattern, and where the interrogating apparatus includes an in-field computer that compares the raw data interrogation pattern produced by an unknown particle with multiple interrogation patterns stored in a known-species-particle memory that contains known interrogation patterns representing particles that are microorganisms of known species that were interrogated in the same or similar interrogating apparatus, including:

a central station and a communication link between said central station and said interrogating apparatus, said central station constructed to send a group of new raw data interrogation patterns representing a new species of microorganism, to said in-field computer and said in-field computer being constructed to add said group of new raw data interrogation patterns to said known-species-particle memory.

5. The system described in claim 4 wherein:

said in-field computer has an unidentified-species memory, and said in-field computer is constructed to store the raw data interrogation patterns of at least those particles which are not found to be a member of said known species in said unidentified-species-memory;

said in-field computer is constructed to determine whether or not a group of said raw data interrogation patterns stored in said unidentified-species memory, and that represent at least a predetermined percent of raw data interrogation patterns stored in said unidentified-species memory, are sufficiently similar to indicate that they are likely to be all of the same species, and to notify said central station when said group that are likely all of the same species, are found.

6. A microscopic particle identification method for use with a system that identifies which, if any, of a predetermined group of known species of microscopic particles whose interrogation patterns are stored in a known-species-particle memory of a computer, that an unknown particle belongs to, by interrogating the unknown particle to produce a raw data interrogation pattern that is unique to the unknown particle, and comparing the raw data interrogation pattern of the unknown particle to interrogation patterns of said predetermined group of known species of particles, including:

transmitting new raw data interrogation patterns of a new species of microscopic particle over a transmission link from a central station to said in-field computer and storing said new interrogation patterns in said known-species-particle memory, and thereafter comparing raw data interrogation patterns of unknown particles to interrogation patterns of a new group of known particles wherein said new group includes the interrogation patterns of said new species of microscopic particle.

7. The method described in claim 6 including:

storing the raw data interrogation patterns of unknown particles and analyzing them to determine whether or not the patterns of a group of said unknown particles are similar enough to indicate the presence of a significant percent of particles that are all of a new species of particles.

* * * * *

UNITED STATES PATENT AND TRADEMARK OFFICE
CERTIFICATE OF CORRECTION

| | | |
|---|---|---|
| PATENT NO. | : 7,057,724 B1 | Page 1 of 1 |
| APPLICATION NO. | : 10/393459 | |
| DATED | : June 6, 2006 | |
| INVENTOR(S) | : Donald Mead and Gregory Quist | |

It is certified that error appears in the above-identified patent and that said Letters Patent is hereby corrected as shown below:

On the title page, item [73] Assignee, change "Institute of Critical Care Medicine, Rancho Mirage, CA (US)" to -- PointSource Technologies, LLC
  Escondido, CA (US) --

Signed and Sealed this
Fifth Day of February, 2013

Teresa Stanek Rea
*Acting Director of the United States Patent and Trademark Office*